United States Patent [19]

Micetich et al.

[11] 4,035,354

[45] July 12, 1977

[54] THIOAMIDES OF BETA-LACTAM ANTIBIOTICS

[75] Inventors: Ronald G. Micetich; Clinton G. Chin; Robert B. Morin, all of Edmonton, Canada

[73] Assignee: Connlab Holdings Limited, Willowdale, Canada

[21] Appl. No.: 571,426

[22] Filed: Apr. 24, 1975

[30] Foreign Application Priority Data

Sept. 11, 1974  Canada .............................. 209225

[51] Int. Cl.² .......................................... C07D 499/44
[52] U.S. Cl. .......................... 260/239.1; 260/243 C
[58] Field of Search ................................. 260/239.1

[56] References Cited

U.S. PATENT DOCUMENTS 3,118,877  1/1964  Perron et al. .................... 260/239.1

*Primary Examiner*—Gerald A. Schwartz
*Attorney, Agent, or Firm*—Weiser, Stapler & Spivak

[57] ABSTRACT

The invention relates to compounds of the formula:

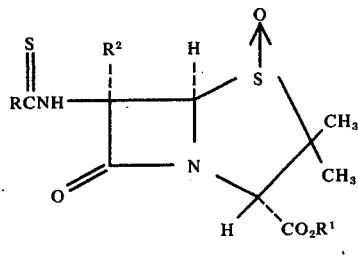

wherein
R stands for
  benzyl,
  phenoxymethyl,
  4-amino-4-carboxy-1-butyl,
  $R^3O-$, $R^3S-$, $R^3R^4N-$ wherein
  $R^3$ is loweralkyl, aryl or arylloweralkyl,
  $R^4$ is hydrogen or $R^3$, and
$R^2$ is hydrogen or methoxy, and
$R^1$ is hydrogen or a cleavable radical such as $-CH_2OCH_3$, loweralkyl, 2,2,2-trichloroethyl, benzyl, p-nitrobenzyl, benzhydryl, phenacyl or trimethylsilyl. The novel compounds are useful intermediates in the preparation of known penicillin and cephalosporin derivatives.

14 Claims, No Drawings

THIOAMIDES OF BETA-LACTAM ANTIBIOTICS

The present invention relates to a group of novel intermediates which are particularly suitable for preparing a number of known penicillin and cephalosporin derivatives.

PRIOR ART

Known commercial cephalosporins such as cephalexin, cephaloglycin, cephaloridine, cephalothin, cefazolin, and cephapirin are obtained by a number of different processes which also involve preparing a variety of intermediates for the respective cephalosporins. Cephalosporin C is deacylated initially (removal of the aminoadipyl moiety) by means of several reported chemical processes to yield 7-aminocephalosporanic acid (7-ACA) which is then reacylated with the appropriate group. In the case of cefazolin (and also cephaloridine) the acetoxy group is replaced by an appropriate moiety in yet another chemical reaction.

As can be appreciated, the relative difficulty and consequently high cost of preparing cephalosporin C has led to a constant search for other methods of preparing cephalosporin antibiotics. One such method which has been discovered involves the use of readily available and low cost penicillins G or V. For example, it is known that cephalexin may be obtained from Penicillins G or V through a multi-step sequence. Unfortunately this procedure is limited practically to the preparation of cephalexin only and so far no method has been devised whereby other cephalosporin antibiotics can also be prepared from Penicillin G or V except through multi-step processes.

It is also known that desacetoxy cephalosporin C can be obtained by fermentation and could possibly be considered as a suitable source for the preparation of any desired cephalosporin antibiotic. Unfortunately so many steps are involved in order to prepare any desired cephalosporin antibiotic, that the industry has not generally considered desacetoxy cephalosporin C as a suitable starting intermediate capable of producing all commercially available cephalosporins.

It is also known that the variety of commercial semisynthetic penicillins became available only after the common intermediate 6-aminopenicillanic acid (6-APA) was discovered. With the advent of 6-APA any commercially available derivative of penicillanic acid which was desired could be obtained through a simple acylation step. In view of knowledge acquired in the 6-APA field, it was felt that the difficulties in preparing commercial cephalosporins might be overcome if 7-aminocephalosporanic acid (7-ACA) could be readily prepared from penicillin derivatives. However it was found that the higher costs involved in preparing 7-ACA, and the number of subsequent chemical reactions required, limited its use to a greater extent as a common intermediate for the preparation of cephalosporins.

In view of the low costs of Penicillins G or V and potentially readily available Penicillin N, or 6-APA, it should be obvious that a great advantage would be derived if an intermediate could be derived therefrom and if this intermediate should prove suitable for preparing a variety of desired cephalosporins in a more expeditious manner. It is felt that the low cost of the penicillins could possibly yield a low cost intermediate capable of reducing the cost of manufacturing any desired cephalosporin antibiotic.

THE INVENTION

In accordance with the present invention, there is now provided a novel low cost intermediate derivable from Penicillin G, N or V or 6-aminopenicillanic acid, which is suitable not only for the preparation of known cephalosporins, but which could also be used for the preparation of novel cephalosporins and penicillins.

The novel intermediates of the present invention are penicillin sulfoxide thioamides II corresponding to the general formula:

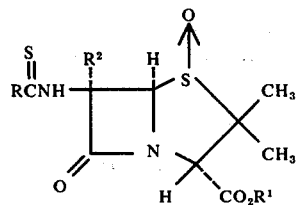

wherein

R stands for benzyl, phenoxymethyl, 4-amino-4-carboxy-1-butyl, $R^3O—$, $R^3S—$, $R^3R^4N—$ wherein $R^3$ is loweralkyl, aryl or arylloweralkyl, $R^4$ is hydrogen or $R^3$, and $R^2$ is hydrogen or methoxy, and $R^1$ is hydrogen or a cleavable radical such as $—CH_2OCH_3$, loweralkyl, 2,2,2-trichloroethyl, benzyl, p-nitrobenzyl, benzhydryl, phenacyl or trimethylsilyl.

The penicillin sulfoxide thioamides II of the present invention where R stands for $R^3O—$, $R^3S—$ and $R^3R^4N—$ may be obtained by thioacylation of 6-aminopenicillanic acid sulfoxide with a thioacylating agent corresponding to the following formulae:

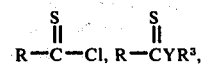

$CS_2/R^3X$, $R^3N=C=S$, $CSCl_2/R^3R^4NH$, wherein $R^3$ is as previously defined, Y is sulfur or oxygen and X is halogen. The thioacylation reaction is carried out in the manner known in the art. It is also possible to obtain the penicillin sulfoxide thioamides II wherein R stands for $R^3O—$, $R^3S—$ or $R^3R^4N—$ by treating a 6-isothiocyanate of penicillanic acid sulfoxide or its esters with an alcohol of the formula $R^3OH$, a thiol of the formula $R^3SH$ or an amine of the formula $R^3R^4NH$.

Alternatively the penicillin sulfoxide thioamides II may be derived from Penicillin G, N or V sulfoxides in which case R is benzyl when starting from Penicillin G, R is phenoxymethyl when starting from Penicillin V and R is 4-amino-4-carboxy-1-butyl when starting from Penicillin N, in which case it is preferred to protect the amino group by acylation and the carboxyl group by esterification. The preparation of the penicillin sulfoxide thioamides II or its esters by this route may be schematically illustrated by reference to Flowsheet I.

__FLOWSHEET I__

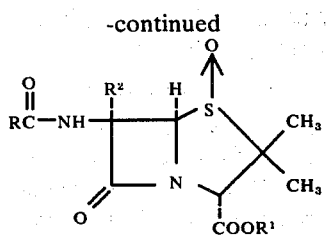

III

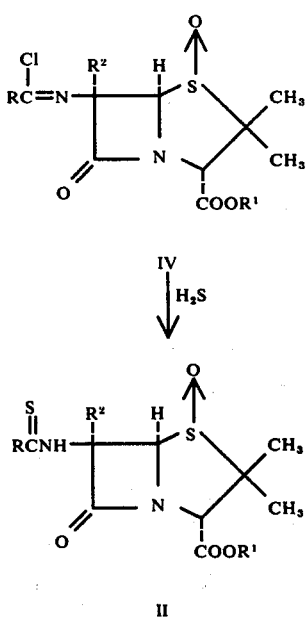

II

More particularly, Penicillin G sulfoxide, protected Penicillin N sulfoxide or Penicillin V sulfoxide III is chlorinated with a suitable agent such as phosphorus pentachloride in the presence of a base such as dimethylaniline or pyridine. Other chlorinating agents such as phosgene can also be used. The chloroimine compound IV is then readily transformed to its corresponding thioamide II by reacton with hydrogen sulfide in the presence of an acid catalyst such as hydrogen chloride or sulfuric acid or the like.

The novel penicillin sulfoxide thioamides II of the present invention may be converted by heating into the 1,2,4-dithiaaz-3-enes I of the general formula:

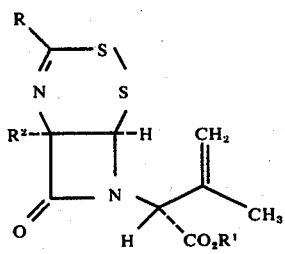

wherein R, $R^1$ and $R^2$ are as previously defined. The reaction is carried out at a temperature of from about 40° to about 180° C. in an organic solvent such as toluene, dioxane, dimethylformamide and similar solvents.

It should be appreciated that the 1,2,4-dithiaaz-3-enes I obtained from the penicillin sulfoxide thioamides of the present invention are useful intermediates for the preparation of cephalosporins. For example, on treatment with sulfenyl halides they provide 3-halocephams which can be converted to the cephem compounds, such as 7-ADCA (7-aminodesacetoxycephalosporanic acid) by methods known to the art.

EXAMPLES

The present invention will be more readily understood by referring to the following Examples which are given only to illustrate the invention rather than limit its scope.

EXAMPLE 1

METHYL 6-PHENOXYTHIOACETAMIDOPENICILLANATE SULFOXIDE II (R = $\phi OCH_2$-, $R^1$ = $CH_3$)

Phosphorus pentachloride (26.4 g., 0.126 mole) was added in one lot to a stirred, cold (−70°) solution of methyl penicillin V sulfoxide (45.0 g., 0.1185 mole) and dimethylaniline (36.3 g., 0.3 moles) in methylene chloride (600 ml), and the mixture stirred for 2½ hrs. at −50° or lower. $H_2S$ is then bubbled into the reaction mixture at −70° and after approximately ½ hr. the mixture becomes a clear yellow from a clear dark brown colour. The $H_2S$ is continued for 1 hr. at −50° and the mixture warmed to 0° by applying an ice bath. The $H_2S$ addition is continued at 0° C. for 1½ hrs, after which the reaction mixture is poured into ice water (750 ml) and the resulting mixture stirred with aqueous sodium bicarbonate (90 g. in 200 ml). The layers were separated and the organic layer extracted sequentially with water (300 ml), aqueous HCl (3 molar, 2 × 300 ml) and salt water (300 ml). The organic layer was dried ($MgSO_4$), filtered and the filtrate concentrated to a yellow powder, 44.5 g., which was estimated to contain about 60% of methyl 6-phenoxythioacetamidopenicillanate sulfoxide from its nmr spectrum.

The crude thioamide was purified by column chromatography over silica gel (Grace Davidson SMR7-1498 grade 951-MS, 450 g.) using chloroform as eluent and collecting about 50 ml fractions. The process was monitored by tlc of the fractions. Fractions 11 to 145 contained the thioamide and were combined and concentrated to give 26.6 g. of the thioamide which was washed with methanol to give 22.8 g. of pure thioamide. An analytical sample was obtained by recrystallization from methanol as white crystals, m.p. 144°–145°.

Analysis: Calcd: C 51.51, H 5.05, N 7.07, S 16.16; Found: C 51.55, H 5.03, N 7.08, S 15.83.

The ir and nmr spectra were in agreement with the assigned structure. The nmr spectrum was quite characteristic and differed appreciably from the starting amide. The nmr ($CDCl_3$) spectrum had signals at $\phi$1.23(s,3H), 1.73(s,3H), gem. $CH_3$; 3.85(s,3H), $COOCH_3$; 4.73(s,1H), $C_3$-H; 4.95(s,2H), -$OCH_2$-; 5.20(d,1H, J 5cps) $C_5$-H; 6.67 to 7.40(m,6H), $C_6H_5$ and $C_6$-H; 9.78(d,1H), -CSNH-.

The methyl penicillin V sulfoxide was collected in later fractions.

EXAMPLE 2

6-PHENOXYTHIOACETAMIDOPENICILLANIC ACID SULFOXIDE II (R = $\phi OCH_2-$, $R^1$ = H)

Anhydrous penicillin V sulfoxide (1.098 g., 3 mmoles, prepared by drying penicillin V sulfoxide at 60° C. under vacuum over $P_2O_5$ to constant weight) and dimethylaniline (1.14 ml., 9 mmoles) were dissolved in dry methylene chloride (20 ml., dried by distillation over $P_2O_5$) and cooled to 0° C. Trimethylchlorosilane (0.418 ml., 3.3 mmoles) was added and the yellow solution stirred for 30 mins at 0° C. The mixture was then cooled to −30° and $PCl_5$ (0.685 g., 3.3 mmoles) added. The mixture was stirred for 3 hours at −35° to −25°, by which time the mixture became a dark green colour. $H_2S$ was then passed through the stirred solution. On contact with $H_2S$, the green colour was immediately discharged. After 30 mins the temperature of the reaction mixture was raised to 0° by placing it in an ice-bath and, after stirring a further 30 mins at this temperature, the $H_2S$ addition was discontinued and nitrogen was passed through the mixture which was diluted with methylene chloride. The mixture was extracted with saturated aqueous sodium bicarbonate (3 times, until the pH of the aqueous layer was 8). The alkaline solution extract was then extracted with ether (4 times) and then acidified to pH 2.0 with hydrochloric acid (3 normal). At this stage some of the compound precipitated. The mixture was extracted with ethyl acetate (3 times). The combined organic extracts were washed with water, dried over $Na_2SO_4$ and taken to dryness to give 0.73 g. of a yellow solid, whose thin layer chromatogram and ir and nmr spectra showed a mixture of the amide and thioamide. The 6-phenoxythioacetamidopenicillanic acid sulfoxide was estimated to be present in about 70% yield from the nmr spectrum. Purification of this thioamide can be effected by column chromatography, using silicic acid.

EXAMPLE 3

6-PHENOXYTHIOCARBAMIDOPENICILLANIC ACID SULFOXIDE II (R = $\phi O$, $R^1$ = H)

Aqueous potassium hydroxide (2 normal) was added slowly to an ice-cold stirred suspension of 6-APA sulfoxide (23.2 g., 0.1 mole) in water (275 ml), until a pH of 8.0. The solution was diluted with THF (125 ml). The solution was stirred in the ice-bath and separate solutions of phenoxythiocarbonyl chloride (17.2 g., 0.1 mole) in THF (50 ml.) and aqueous KOH (2 normal) added by two separate dropping funnels at such a rate as to maintain the pH constant at 8.0. The reaction mixture was stored in a refrigerator overnight and then extracted with ethyl acetate (2 × 250 ml.). The water layer was covered with ethyl acetate (150 ml.) in an ice-bath and the pH adjusted to 1.5 with hydrochloric acid (12 normal). The layers were separated and the aqueous layer extracted with ethyl acetate (2 × 125 ml). The combined ethyl acetate layers were dried over $MgSO_4$, concentrated and dried under vacuum to yield 34.3 g. (92%) of the crude 6-phenoxythiocarbamidopenicillanic acid sulfoxide as a yellow brown foam.

The product was further purified by stirring with ether (3 × 25 ml per gram of crude), filtering and discarding the insoluble yellow solid. The ether filtrate was treated with decolorizing charcoal, filtered and concentrated to a small volume. The white solid that separated (about 50% recovery) had m.p. 153°–156° (decomp) and nmr and ir spectra in agreement with the proposed structure.

Analysis: Calcd. C 48.91, H 4.34, N 7.60, S 17.39; Found C 48.63, H 4.68, N 7.41, S 17.09.

EXAMPLE 4

METHOXYMETHYL 6-PHENOXYTHIOCARBAMIDOPENICILLANATE SULFOXIDE II (R = $\phi O$, $R^1$ = $CH_3OCH_2$-)

Chloromethylmethyl ether (2.66 g., 0.033 mole) was added slowly to an ice-cold stirred solution of 6-APA sulfoxide (6.96 g., 0.03 mole) and triethylamine (6.66 g., 0.066 mole) in methylene chloride (50 ml) and the reaction mixture stirred in the ice-bath for ½ hr. Phenoxythiocarbonyl chloride (5.7 g., 0.033 mole) was then added slowly, when a mild exothermic reaction (the temp rising to 5°) occurred. The reaction mixture was stirred an additional hour, by which time the yellow solution containing a moderate amount of solid had become almost clear and black. The reaction mixture was washed with water (2 × 30 ml.), dried ($MgSO_4$ with added decolorizing carbon) filtered and concentrated to 11 g. (88.7%) of a brown foam. The solid was stirred with ethyl acetate (200 ml) for ½ hr and filtered and the solid washed with ethyl acetate. The combined filtrates on concentration gave 8.4 g. (67.7%) of methoxymethyl 6-phenoxythiocarbamidopenicillanate sulfoxide as a yellow foam whose ir and nmr spectra were in agreement with the assigned structure.

EXAMPLE 5

METHYL 6-METHYLDITHIOCARBAMIDOPENICILLANATE SULFOXIDE II (R = $CH_3S$, $R^1$ = $CH_3$) and 6-METHYLDITHIOCARBAMIDOPENICILLANIC ACID SULFOXIDE II (R = $CH_3S$, $R^1$ = H)

Carbon disulfide (3.35 g., 0.044 mole) was added to an ice-cold stirred solution of 6-APA sulfoxide (9.28 g., 0.04 mole), and triethylamine (8.5 g., 0.084 mole) in dry DMF (25 ml). After ½ hour stirring in the ice-bath, methyl iodide (12.4 g., 0.088 mole) was added, the mixture stirred an additional hour in the ice-bath and then stirred at ambient temperature overnight (16 hours). The solution was poured, with vigorous stirring into excess water when a sticky solid separated. The solid was taken up in chloroform, the organic layer washed with water (3 × 50 ml), dried over $MgSO_4$ with decolorizing carbon, filtered, and the filtrate concentrated to a brown foam 8.6 g., (62%). The nmr and ir spectra indicated that the desired compounds were present in the product. A tlc using ether as the developing solvent and iodine for visualizing the components, indicated the presence of at least four components.

The crude product (5.0 g.) was purified by chromatography on silicic acid (250 g.) using ether as eluent and collecting fractions (10 ml.). White crystals appeared in many of the fractions 48–82, which all showed the same component to be present by tlc. These crystals, from the nmr spectrum were a mixture of the methyl 6-methyldithiocarbamidopenicillanate sulfoxide and 6-methyldithiocarbamidopenicillanic acid sulfoxide in a ratio of about 2:1. These fractions were combined and concentrated to give 2.7 g. of a brown foam whose nmr spectrum indicated a mixture of the methyl ester and the acid in the ratio of about 1:1. A partial separation could be effected with ether.

The methyl ester was obtained pure by treating a solution of the mixture in chloroform with aqueous sodium bicarbonate, drying the organic layer and concentrating, whereby the methyl ester was obtained as a white foam, m.p. 138°–142°. The ir and nmr spectra were in agreement with the assigned structure and the C,H values were within 0.4% of the calculated values.

Analysis: Calcd: C 39.28, H 4.76; Found: C 39.06, H 5.09.

A high resolution mass spectral analysis of this compound gave a mass of 336.0268 for the parent ion. Calculated for $C_{11}H_{16}N_2S_3{}^{32}O_4$ is 336.0273.

An attempt to recover the acid from the bicarbonate layer was not successful.

EXAMPLE 6

METHOXYMETHYL 6-METHOXYMETHYLDITHIOCARBAMIDOPENICILLANATE SULFOXIDE II (R = $CH_3OCH_2S$ and $R^1 = CH_3OCH_2-$)

Carbon disulfide (1.7 g., 0.022 moles) was added to an ice-cold, stirred solution of 6-APA sulfoxide (4.65 g., 0.02 mole) and triethylamine (4.9 g., 0.048 mole) in methylene chloride (65 ml), and the mixture stirred ½ hour in the ice-bath and 1 hour at room temperature. The mixture was cooled in an ice-bath and chloromethylmethyl ether (3.5 g., 0.044 mole) added dropwise over ½ hour. The reaction mixture was stirred an additional hour in the ice-bath, then at room temperature for 1 hour, finally cooled and washed rapidly with ice-water (3 × 20 ml). The organic layer was dried (MgSO₄) and concentrated to 6.1 g. of the methoxymethyl 6-methoxymethyldithiocarbamidopenicillanate sulfoxide as a sticky yellow solid. The ir and nmr spectrum of this compound were in agreement with the assigned structure. The compound underwent rapid hydrolysis with water and became quite sticky on exposure to the air.

EXAMPLE 7

METHOXYMETHYL 6-METHYLDITHIOCARBAMIDOPENICILLANATE SULFOXIDE II (R = $CH_3S$, $R^1 = CH_3OCH_2-$)

Chloromethylmethyl ether (2.5 g., 0.03 mole) was added to an ice-cold, stirred solution of 6-APA sulfoxide (6.9 g., 0.03 mole), and triethylamine (9.1 g., 0.09 mole) in methylene chloride, and the reaction mixture stirred for an additional ½ hour in the ice-bath. A mixture of carbon disulfide (2.4 g., 0.03 mole) and methyl iodide (8.6 g., 0.06 mole) in methylene chloride (20 ml.) was added slowly to the cold (10° C) stirred reaction mixture, which was then stirred an additional 2 hours at ambient temperature. The mixture was stirred with water. (It was necessary to add an excess of ethyl acetate to break the emulsion). The separated organic layer was washed with water (2 times), dried over MgSO₄ with decolorizing carbon, filtered through celite, and the filtrate concentrated to a light yellow foam weighing 3.7 g. (34%) which was the methoxymethyl 6-methyldithiocarbamidopenicillanate sulfoxide.

EXAMPLE 8

TRIETHYLAMMONIUM 6-METHYLAMINOTHIOCARBAMIDOPENICILLANATE SULFOXIDE II (R = $CH_3NH$, $R^1 = (C_2H_5)_3NH$)

Methylisothiocyanate (4.1 g., 0.055 mole) was added to an ice-cold, stirred solution of 6-APA sulfoxide (11.6 g., 0.05 mole), and triethylamine (11.1 g., 0.11 mole) in methylene chloride. The reaction mixture was stirred an additional hour in the ice-bath, then for 2 hours at ambient temperature, then treated with decolorizing charcoal, filtered through celite and taken to dryness. The resulting yellow foam was triturated with ether, filtered, washed with ether and dried at the pump to provide 19.7 g. (97%) of a flesh-colored powder which was the triethylammonium 6-methylaminothiocarbamidopenicillanate sulfoxide. The ir and nmr spectra of the product were in agreement with the assigned structure.

The triethylammonium salts were converted to esters, such as the methyl esters, before the thermolysis to the 1,2,4-dithiaaz-3-enes. It is also possible to convert them to the trimethylsilyl esters prior to thermolysis.

EXAMPLE 9

TRIETHYLAMMONIUM 6-PHENYLAMINOTHIOCARBAMIDOPENICILLANATE SULFOXIDE II (R = $\phi NH$, $R^1 = (C_2H_5)_3NH$)

Triethylammonium 6-phenylaminothiocarbamidopenicillanate sulfoxide was made in the same way as in Example 8, by the action of phenylisothiocyanate 6-APA sulfoxide in the presence of triethylamine. The compound was obtained as a pale yellow powder, m.p. 145°–148° (decomp) in 100% yield. The ir and nmr spectra were in agreement with the assigned structure.

The triethylammonium salts were converted to esters, such as the methyl esters, before the thermolysis to the 1,2,4-dithiaaz-3-enes. It is also possible to convert them to the trimethylsilyl esters prior to thermolysis.

EXAMPLE 10

METHYL 4-PHENOXYMETHYLAZETIDINONE[3,4-e][1,2,4]DITHIAAZ-3-ENE-1-ISOPROPENYLACETATE

A solution of methyl 6-phenoxythioacetamidopenicillanate sulfoxide from Example 1 (1.0 g., 2.52 mmoles) in dry (distilled over LiAlH₄) dioxane (500 ml) was heated under reflux in a dry N₂ atmosphere using a Soxhlet extractor packed with MgSO₄, in an oil bath maintained at 135°, for 4 hours. The solution was then concentrated to dryness under reduced pressure to provide the title compound. The ir and nmr spectra were in agreement with the assigned structure. A high resolution mass spectral analysis of this compound gave a mass of 378.0712 for the parent ion. Calculated for $C_{17}H_{18}N_2S_2{}^{32}O_4$ is 378.0702.

In a similar manner using:
methoxymethyl 6-phenoxythiocarbamidopenicillanate sulfoxide,
methyl 6-methyldithiocarbamidopenicillanate sulfoxide,
methoxymethyl 6-methoxymethyldithiocarbamidopenicillanate sulfoxide,
methoxymethyl 6-methyldithiocarbamidopenicillanate sulfoxide,
methyl 6-methylaminothiocarbamidopenicillanate sulfoxide, and
methyl 6-phenylaminothiocarbamidopenicillanate sulfoxide, the latter two compounds being obtained from the triethylammonium salts, it is possible to obtain the following compounds, methoxymethyl 4-phenoxyazetidinone[3,4-e][1,2,4]dithiaaz-3-ene-1-isopropenylacetate,
methyl 4-thiomethylazetidinone[3,4-e][1,2,4]dithiaaz-3-ene-1-isopropenylacetate,
methoxymethyl 4-thiomethoxymethylazetidinone[3,4-e][1,2,4]-dithiaaz-3-ene-1-isopropenylacetate,
methoxymethyl 4-thiomethylazetidinone[3,4-e][1,2,4]dithiaaz-3-ene-1-isopropenylacetate,
methyl 4-methylaminoazetidinone[3,4-e][1,2,4]dithiaaz-3-ene-1-isopropenylacetate, and
methyl 4-phenylaminoazetidinone[3,4-e]dithiaaz-3-ene-1-isopropenylacetate.

EXAMPLE 11

4-PHENOXYAZETIDINONE[3,4-e][1,2,4]DITHIAAZ-3-ENE-1-ISOPROPENYLACETIC ACID

A solution of 6-phenoxythiocarbamidopenicillanic acid sulfoxide from Example 3 (10 g.) in dry dioxane (1.6 liters) was heated with stirring under reflux in an oil bath maintained at 120° for 4 hours. The solution was then concentrated to dryness under vacuum when 9.2 g. of a brown powder was obtained. This material could be purified by fractionation using ether, when the desired compound was obtained as an amorphous white powder, m.p. 144°–146° (decomp). The ir and nmr spectra are in agreement with the assigned structure. A high resolution mass spectral analysis of this compound gave a mass of 350.0404 for the parent ion, that calculated for $C_{15}H_{14}N_2S_2{}^{32}O_4$ being 350.0396.

In a similar manner using:
6-phenoxythioacetamidopenicillanic acid sulfoxide, and
6-methyldithiocarbamidopenicillanic acid sulfoxide, it is possible to obtain the following compounds:
4-phenoxymethylazetidinone[3,4-e][1,2,4]dithiaaz-3-ene-1-isopropenylacetic acid, and
4-thiomethylazetidinone[3,4-e][1,2,4]dithiaaz-3-ene-1-isopropenylacetic acid.

EXAMPLE 12

TRIMETHYLSILYL 4-PHENOXYAZETIDINONE[3,4-e][1,2,4]DITHIAAZ-3-ENE-1-ISOPROPENYLACETATE I (R = $\phi$O, R$^1$ = SiMe$_3$, R$^2$ = H) and the FREE ACID I (R = $\phi$O, R$^1$ = H, R$_2$ = H)

6-Phenoxythiocarbamidopenicillanic acid sulfoxide (1.0 g., 0.0027 mole from Example 3), and bis-(trimethylsilyl)-trifluoroacetamide (0.8 g., 0.0029 mole), were stirred in toluene (100 ml) at room temperature until solution was complete (about 45 mins.).

The resulting solution was heated under reflux in a nitrogen atmosphere with a Dean-Stark trap, in an oil bath maintained at 130° for 1.5 hours. [The reaction was monitored by nmr spectroscopy on the residues from aliquots taken periodically from a similar reaction and it was found that in about 1.5 hours, the desired reaction was complete]. Concentration of the reaction mixture under anhydrous conditions gave the trimethylsilyl ester as a gum.

The free acid could be conveniently obtained by treating the toluene solution with charcoal, filtering through celite, and concentrating. The residual gum is triturated repeatedly with moist ether and concentrated to a yellow powder. The ir and nmr spectra were in agreement with the assigned structures.

In a similar manner using:
6-phenoxythioacetamidopenicillanic acid sulfoxide (from Example 2),
6-methyldithiocarbamidopenicillanic acid sulfoxide,
triethylammonium 6-methylaminothiocarbamidopenicillanate sulfoxide, and
triethylammonium 6-phenylaminothiocarbamidopenicillanate sulfoxide, it is possible to obtain:
trimethylsilyl 4-phenoxymethylazetidinone[3,4-e][1,2,4]-dithiaaz-3-ene-1-isopropenylacetate,
4-phenoxymethylazetidinone[3,4-e][1,2,4]dithiaaz-3-ene-1-isopropenylacetic acid,
trimethylsilyl 4-thiomethylazetidinone[3,4-e][1,2,4]dithiaaz-3-ene-1-isopropenylacetate,
4-thiomethylazetidinone[3,4-e][1,2,4]dithiaaz-3-ene-1-isopropenylacetic acid,
trimethylsilyl 4-methylaminoazetidinone[3,4-e][1,2,4]dithiaaz-3-ene-1-isopropenylacetate,
4-methylaminoazetidinone[3,4-e][1,2,4]dithiaaz-3-ene-1-isopropenylacetic acid,
trimethylsilyl 4-phenylaminoazetidinone[3,4-e][1,2,4]dithiaaz-3-ene-1-isopropenylacetate, and
4-phenylaminoazetidinone[3,4-e][1,2,4]dithiaaz-3-ene-1-isopropenylacetic acid.

In the case of the triethylammonium salts, the reaction with trimethylsilyl chloride offers a convenient route to the trimethylsilyl esters.

EXAMPLE 13

CONVERSION OF 4-PHENOXYAZETIDINONE[3,4-e][1,2,4]DITHIAAZ-3-ENE-1-ISOPROPENYLACETIC ACID TO 7-AMINODESACETOXYCEPHALOSPORANIC ACID (7-ADCA)

A solution of methanesulfenyl chloride was prepared by adding sulfuryl chloride (3.0 g., 0.022 mole) dropwise to a stirred, cold (−20°) solution of dimethyl disulfide (2.1 g., 0.022 mole) in methylene chloride (30 ml) and stirring for about 15 mins. The solution was stored in a freezer and used within about an hour of preparation.

4-Phenoxyazetidinone[3,4-e][1,2,4]dithiaaz-3-ene-1-isopropenylacetic acid (0.5 g., 1.43 mmole) was dissolved in methylene chloride (25 ml) and the solution cooled to −60°. The freshly prepared methanesulfenyl chloride solution (1.2 ml., 1.43 mmole) was added to the stirred solution and the mixture left stirring at −60° for 1 hour and then allowed to reach 0° C. It was stirred at this temperature for 3 hours and then concentrated under vacuum to give 0.5 g. of a yellow-brown foam. The foam (0.1 g.) was stirred with 80% formic acid (2 ml) and the mixture stirred at ambient temperature overnight. The solution was extracted with ether, after dilution with water, and the aqueous layer concentrated by lyophilization. The residue on thin layer chromatography gave a spot with the same Rf value as 7-ADCA.

We claim:
1. A penicillin sulfoxide thioamide of the formula

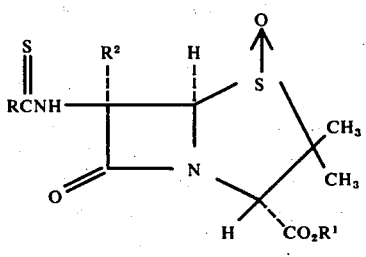

wherein

R is benzyl, phenoxymethyl, 4-amino-4carboxy-1-butyl, $R^3O-$, $R^3S-$, $R^3R^4N-$ wherein $R^3$ is loweralkyl or, phenyl, $R^4$ is hydrogen or $R^3$, and $R^1$ is hydrogen or a conventional cleavable radical selected from the group consisting of $-CH_2OCH_3$, loweralkyl, 2,2,2-trichloroethyl, benzyl, p-nitrobenzyl, benzyhydryl, phenacyl or trimethylsilyl and $R^2$ is hydrogen or methoxy.

2. The compound of claim 1, which is the methyl 6-phenoxythioacetamidopenicillanate sulfoxide.

3. The compound of claim 1, which is the 6-phenoxythioacetamidopenicillanic acid sulfoxide.

4. The compound of claim 1, which is the methoxymethyl 6-phenoxythiocarbamidopenicillanate sulfoxide.

5. The compound of claim 1, which is the methyl 6-methyldithiocarbamidopenicillanate sulfoxide.

6. The compound of claim 1, which is the 6-methyldithiocarbamidopenicillanic acid sulfoxide.

7. The compound of claim 1, which is the methoxymethyl 6-methoxymethyldithiocarbamidopenicillanate sulfoxide.

8. The compound of claim 1, which is the methoxymethyl 6-methyldithiocarbamidopenicillanate sulfoxide.

9. The compound of claim 1, which is the triethylammonium 6-methylaminothiocarbamidopenicillanate sulfoxide.

10. The compound of claim 1, which is the triethylammonium 6-phenylaminothiocarbamidopenicillanate sulfoxide.

11. The compound of claim 1, which is the 6-phenoxythiocarbamidopenicillanic acid sulfoxide.

12. The compound of claim 1, wherein $R^1$ is loweralkyl.

13. The compound of claim 12, wherein $R^1$ is methyl.

14. The compound of claim 1, wherein R is phenoxymethyl.

* * * * *